(12) United States Patent
Culp et al.

(10) Patent No.: US 7,604,181 B2
(45) Date of Patent: Oct. 20, 2009

(54) SYSTEM FOR PROCESSING MASS-FABRICATED ITEMS WITH THREE-DIMENSIONAL CODES

(75) Inventors: James C. Culp, Pleasanton, CA (US); Craig E. Farren, Livermore, CA (US); Steven Shifman, San Ramon, CA (US)

(73) Assignee: Align Technology, Inc., Santa Clara, CA (US)

( * ) Notice: Subject to any disclaimer, the term of this patent is extended or adjusted under 35 U.S.C. 154(b) by 243 days.

(21) Appl. No.: 11/617,193

(22) Filed: Dec. 28, 2006

(65) Prior Publication Data

US 2008/0159798 A1    Jul. 3, 2008

(51) Int. Cl.
*G06K 19/06* (2006.01)

(52) U.S. Cl. .................. 235/494; 235/462.01; 235/385; 433/203.1

(58) Field of Classification Search .................. 235/385, 235/439, 462.01, 494, 474, 475, 479; 433/203.1
See application file for complete search history.

(56) References Cited

U.S. PATENT DOCUMENTS 5,660,305 A * 8/1997 Lasher et al. ............... 221/206
5,677,522 A   10/1997 Rice et al.
5,975,893 A   11/1999 Chishti et al.
6,976,627 B1  12/2005 Culp et al.
2005/0082703 A1  4/2005 Wrosz
2005/0199724 A1* 9/2005 Lubow .................. 235/462.01
2006/0038021 A1* 2/2006 Cantwell et al. ............ 235/487

FOREIGN PATENT DOCUMENTS

GB         2326003      12/1998

\* cited by examiner

*Primary Examiner*—Seung H Lee
*Assistant Examiner*—Christle I Marshall
(74) *Attorney, Agent, or Firm*—Klein, O'Neill & Singh, LLP

(57) ABSTRACT

In the processing of mass-produced items that include a three-dimensional code formed therein, a system is provided for automating certain post-manufacturing processing steps. The system includes a printing mechanism that applies ink to the three-dimensional code to form an optically-readable code; a code-reading mechanism that reads the optically readable code and transmits a signal indicative of the code to a database that may be employed for tracking the processed items; and a transport mechanism that moves the items from the printing mechanism to the code-reading mechanism. In one embodiment, the system also includes a liquid agent application mechanism that applies a liquid agent to the items after the optically-readable code is formed. The transport mechanism includes a plurality of pallets on which the items are placed for processing, and that is operable to move the pallets sequentially to the several processing mechanisms.

28 Claims, 10 Drawing Sheets

US 7,604,181 B2

SYSTEM FOR PROCESSING MASS-FABRICATED ITEMS WITH THREE-DIMENSIONAL CODES

CROSS-REFERENCE TO RELATED APPLICATION

Not Applicable

FEDERALLY SPONSORED RESEARCH OR DEVELOPMENT

Not Applicable

BACKGROUND OF THE INVENTION

1. Field of the Invention

The present invention relates to the field of manufacturing mass-fabricated items. More specifically, it relates to a system and method for automating a series of post-manufacturing processing steps for mass-fabricated items that are provided with three-dimensional codes formed therein, such as molds used to fabricate plastic dental aligners.

2. Background of the Invention

In the production of mass-customized items, the ability to identify individual items is important. One example of mass-customized items is plastic orthodontic alignment appliances, as described, for example, in U.S. Pat. No. 5,975,893 and U.S. Patent Application Publication 2005/0082703, both of which are commonly assigned to the assignee of the subject invention, and the disclosures of which are both incorporated herein by reference. Other examples are prosthetic devices, form-fitting hearing aids, and athletic equipment (such as pads and protectors).

Plastic orthodontic appliances, of the type disclosed in the above-referenced documents, are made as a set of incremental position adjustment appliances that are used to realign or reposition a patient's teeth. The series of incremental position adjustment appliances is custom made for each patient during the fabrication process.

The fabrication process starts with a practitioner (e.g., a dentist) making impressions or casts of the upper and lower dental arches of a patient. The impressions or casts are then sent by the dentist to an orthodontic appliance manufacturing facility. The manufacturing facility creates a treatment file from the impressions or casts that includes the treatment information for the patient. Treatment information includes the number of stages (i.e. each appliance in the series of incremental position adjustment appliances represents a stage) for both the upper and lower jaws that are required for repositioning the patient's teeth, as well as how the patient's teeth move during each stage. The treatment file is then sent to the dentist for approval. Upon approval, the manufacturing facility generates 3D CAD models or images of molds for making the appliances using the treatment file, and then creates the molds using a rapid prototyping process, such as, for example, stereolithography (SLA). The molds are then used to fabricate the appliances. Because each aligner is associated with a unique mold on which the aligner is fabricated, for the purposes of this disclosure, the molds themselves are considered to be mass-fabricated custom items.

The SLA process is performed in SLA machines that build polymeric molds from the CAD images or models. Typically, a mass-customized item is identified by encoding item identification data into a multi-dimensional barcode and using an SLA apparatus to make the part with the multi-dimensional (i.e., three-dimensional) barcode embedded therein. See, for example, U.S. Pat. No. 6,976,627, commonly assigned to the assignee of the subject invention, the disclosure of which is incorporated herein by reference.

Ink is manually applied to the barcode with a marker so that a barcode reader can accurately read the information encoded therein. Next, a release agent is manually sprayed onto the molds so that the aligners can be easily separated from the molds. These process steps involve laborious manual operations, and therefore entail substantial costs and time to produce the items. Accordingly, there is a need for an efficient system and method to improve productivity by automating as many of these steps as possible.

SUMMARY OF THE INVENTION

Broadly, the present invention, in a first aspect, is a system for the automated processing of items, each of which incorporates information encoded in a three-dimensional code formed in the item, wherein the system comprises a printing mechanism operable to apply an ink medium to the three-dimensional code to form an optically-readable code; a code-reading mechanism operable to read the optically readable code and to transmit a signal indicative of the code to a database; and a transport mechanism operable to transport the items from the printing mechanism to the code-reading mechanism.

In a second aspect, the present invention may be broadly defined as a method for the automated processing of items, each of which incorporates information encoded in a three-dimensional code formed in the item, wherein the method comprises (1) applying an ink medium to the three-dimensional code to render the code optically readable; (2) optically scanning the optically readable code to create an electronic signal indicative of the code; and (3) transmitting the signal to a computer database.

BRIEF DESCRIPTION OF THE DRAWINGS

The foregoing features and other features of the present invention will now be described with reference to the drawings of a preferred embodiment. In the drawings, the same components have the same reference numerals. The illustrated embodiment is intended to illustrate, but not to limit the invention. The drawings include the following Figures.

DETAILED DESCRIPTION OF THE INVENTION

The present invention provides a system and method for processing items that incorporate information encoded in a three-dimensional coded data matrix formed in the items, such as, for example, mass-produced customized items. The system of the present invention, in a preferred embodiment, is controlled by a software algorithm executed by a computer system through a local area network, of conventional design, operation, and architecture. In the following detailed description of the invention, the invention is described primarily in context of a method for processing dental aligner molds. However, it should be understood that the system and process of the present invention may be employed in the processing of various other types of mass-customized items and other items that carry encoded information in a three-dimensional coded data matrix, such as a three-dimensional barcode.

Mass-customized items, such as dental aligner molds, may be made by a stereolithography (SLA) apparatus, as is known in the art. Items such as molds may be formed in the SLA process with a three-dimensional barcode formed on the surface of the item. In the case of dental aligner molds, the barcode is encoded with information that may include, for example, the identity of the patient associated with the mold, which stage in the series of stages the mold represents, and whether the mold is for the upper or lower dental arch. Once the molds have been completed by the SLA process, they are sent to an automated processing system for post-manufacture processing that includes a number of discrete steps.

Figure 1:
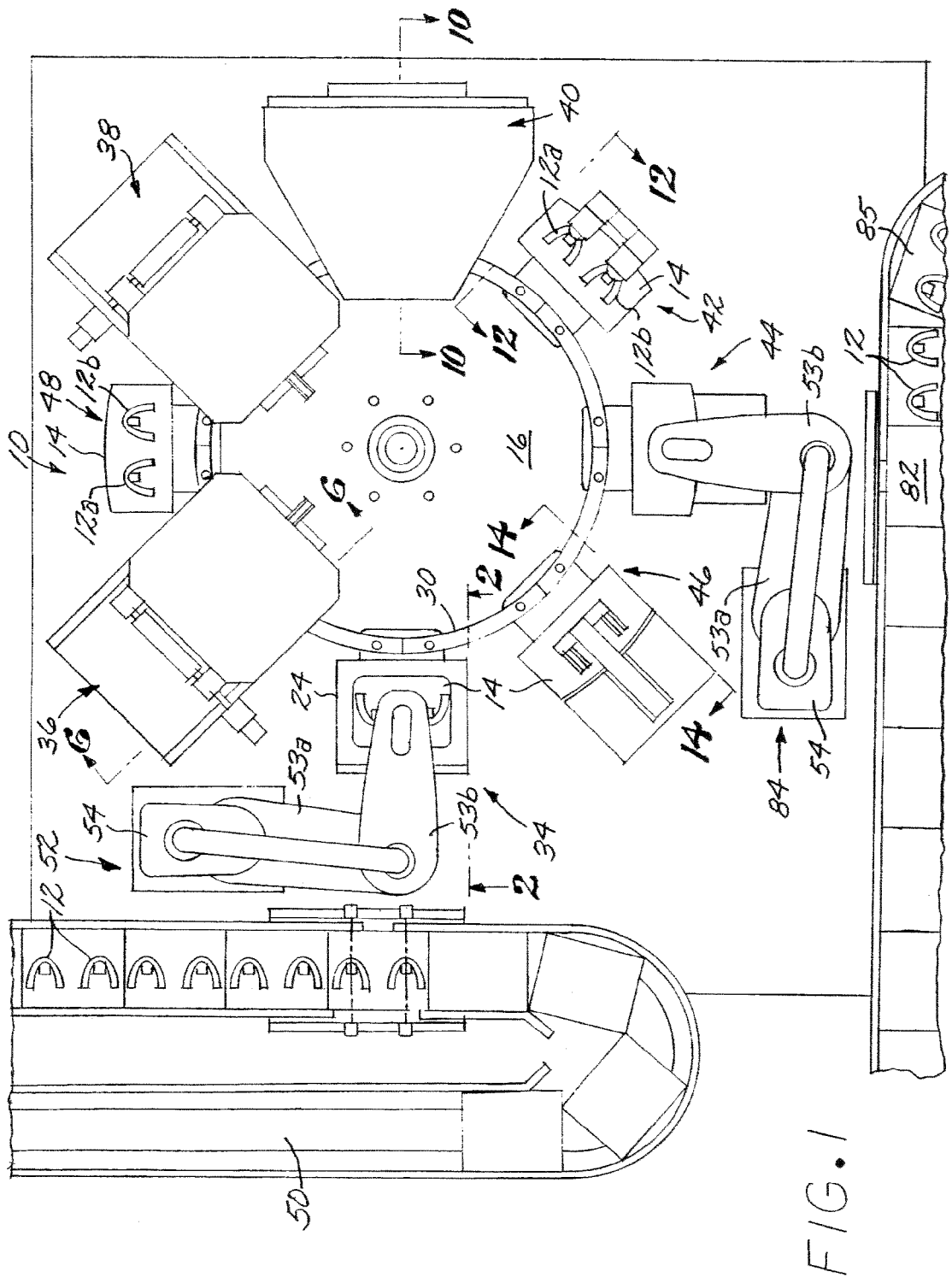
FIG. 1 is a top plan view of an automated processing systems for processing information encoded items, in accordance with a preferred embodiment of the present invention.
Figure 2:
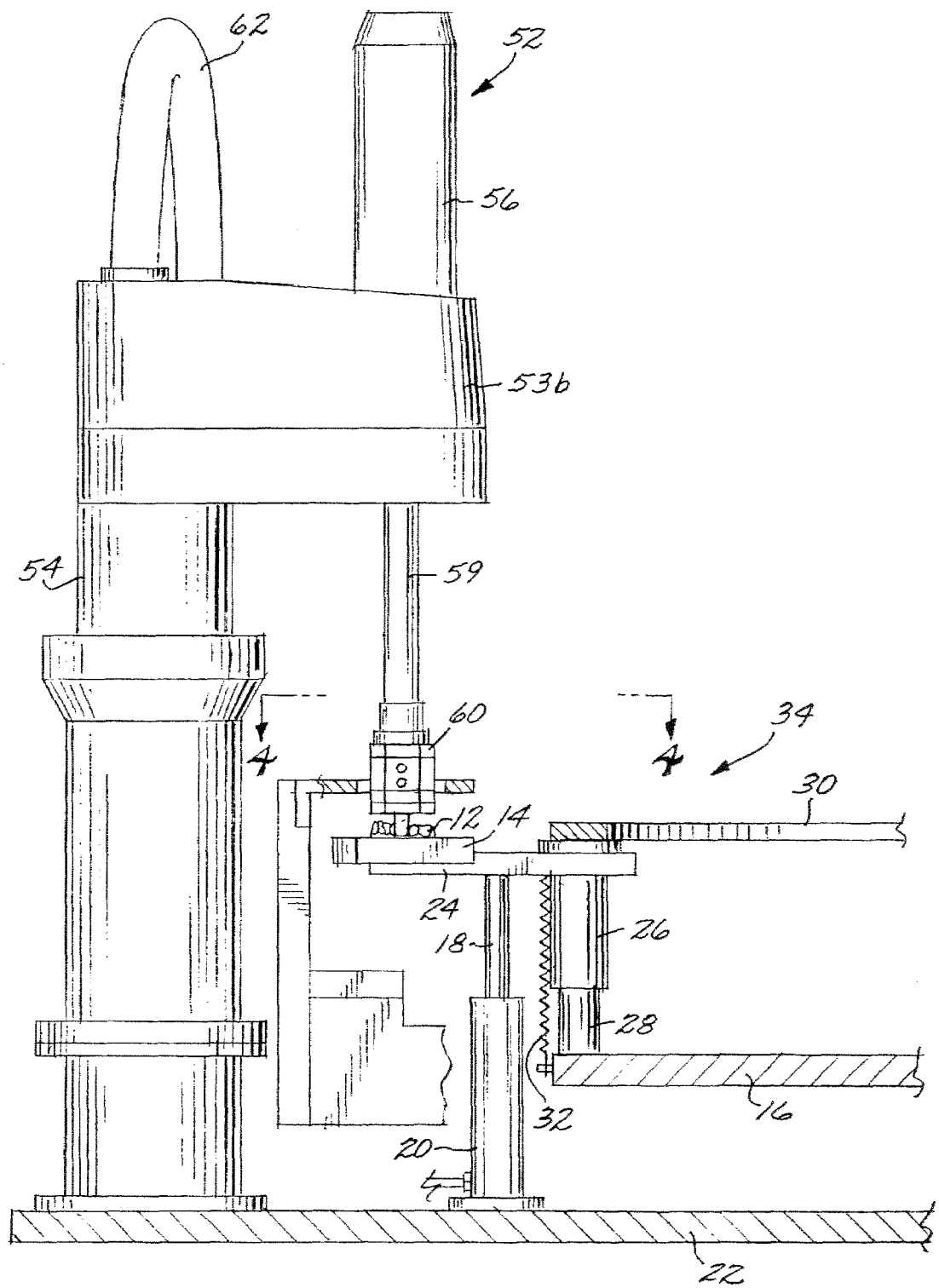
FIG. 2 is an elevational view, partly in cross-section, of a loading station of the automated processing system, taken along line 2-2 of FIG. 1.
Figure 3:
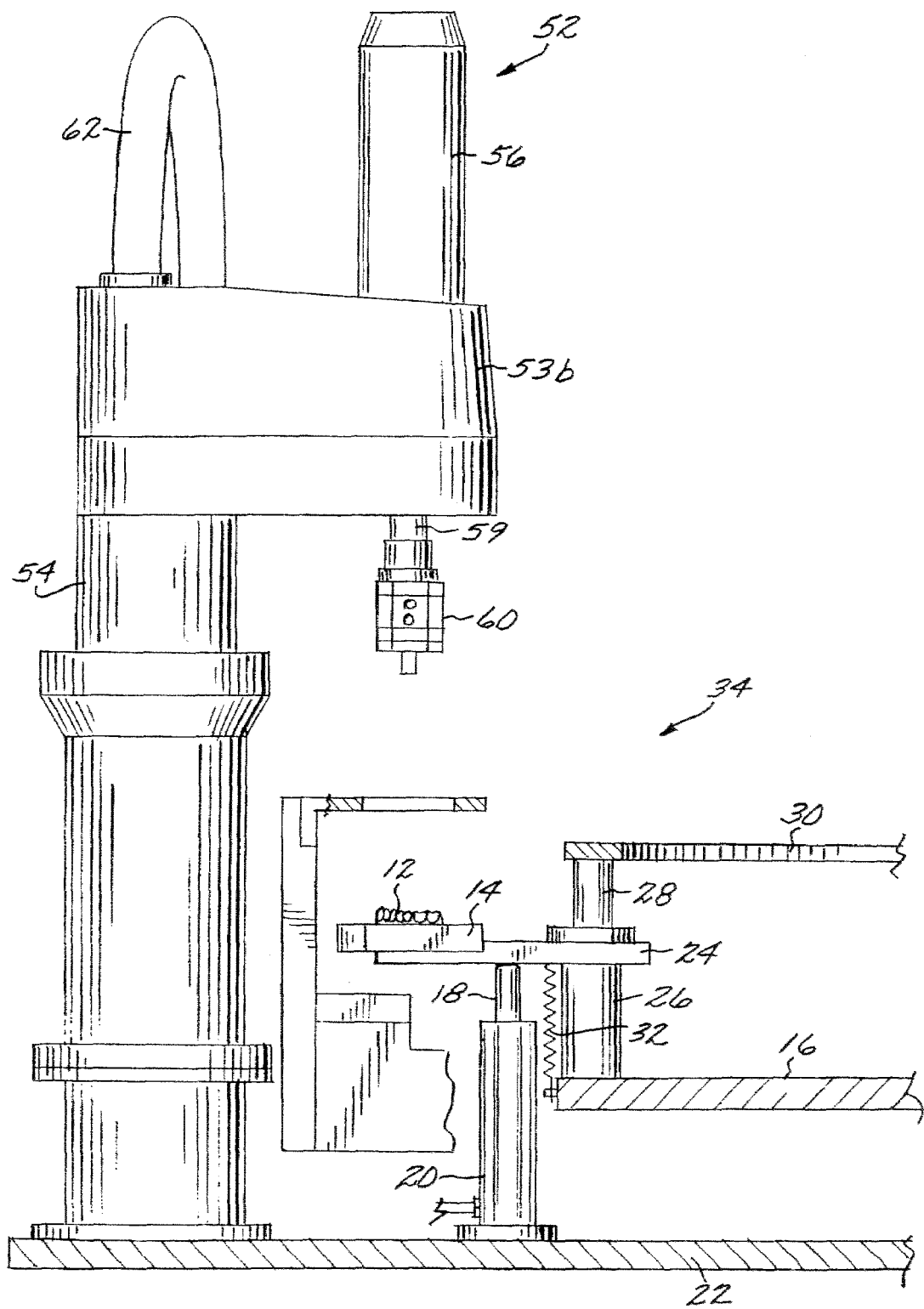
FIG. 3 is a view similar to that of FIG. 2, showing the loading station of FIG. 2 in a retracted position.
Figure 4:
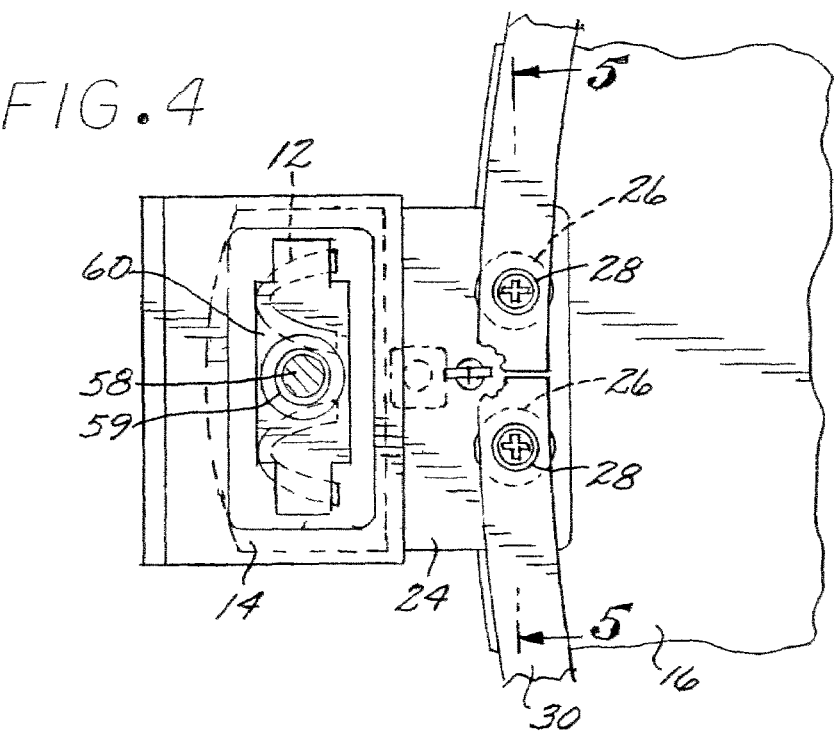
FIG. 4 is a cross-sectional view of the loading station, taken along line 4-4 of FIG. 2.
Figure 5:
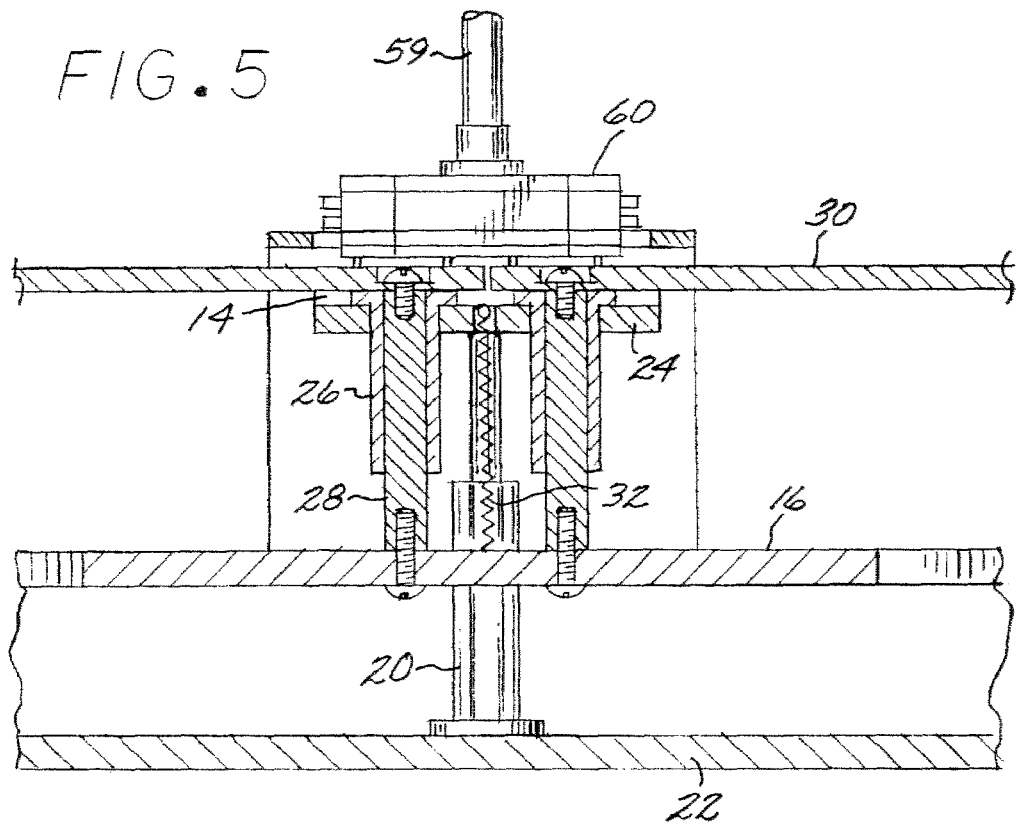
FIG. 5 is a cross-sectional view of the loading station, taken along line 5-5 of FIG. 4.

FIG. 1 is a top plan view of the automated processing system or apparatus 10 for processing mass-customized items 12, particularly dental aligner molds, in accordance with a preferred embodiment of the present invention. The processing system or apparatus 10 comprises a plurality of small platforms or pallets 14 that are attached by a pneumatic pallet-raising mechanism (described below) to a turntable or turret 16 that rotates the pallets 14 sequentially to a plurality of processing stations (described below) to perform a sequence of processing functions in a continuous fashion.

The pallet-raising mechanism, as shown in FIGS. 2-6, comprises a piston or rod 18, actuated by a pneumatic cylinder 20 supported on a base 22 on which the turret or turntable 16 is mounted. One such pallet-raising mechanism 18, 20 is advantageously provided at each station. The upper end of the piston or rod 18 engages the bottom surface of a platform 24 on which the pallet 14 is carried. The platform 24, in turn, is fixed to the turret or turntable 16 to rotate therewith. Specifically, each platform 24 is fixed to the upper end of a pair of outer sleeves 26, each of which is slidably carried on a coaxial tube or rod 28, the bottom end of which is fixed to the turntable 16, and the upper end of which is fixed to a support ring 30 disposed above the turntable 16. By means of the pallet-raising mechanism 18, 20, each pallet 14 may be raised or lifted relative to the turret or turntable 16 to an operational position at several of the stations, as will be described below, and then lowered to a travel position between stations. A spring 32 is fixed between the platform 24 and the turntable 16 to maintain the engagement between the platform 24 and the turntable 16 when the platform 24 is lowered.

It will be appreciated that the pallet raising mechanism described herein is exemplary only. Other types of mechanisms for raising and lowering the pallets 14 relative to the turntable or platform 16 will suggest themselves to those skilled in the arts, such as, for example, electrical and electromagnetic mechanisms.

The stations, as described below, advantageously include the following: a loading station 34, a first printing station 36, a second printing station 38, a liquid agent application station 40, a barcode reading station 42, an unloading station 44, and a pallet cleaning station 46. There may also be an extra or "idle" station 48 (advantageously, but not necessarily, located between the first printing station 36 and the second printing station 38) that may be used to perform an additional step that may be desirable or necessary in a particular application. In some applications, the liquid agent application station 40 may not be necessary. In such applications, it may be rendered inoperable or omitted altogether.

The items 12 may be transported by a first conveyor line or belt 50 to the loading station 34 for loading the items 12 onto a pallet 14. FIGS. 2-6 show the loading station 34 as employed in an exemplary embodiment of the invention. The loading station 34 includes a first robotic pick and place mechanism 52 that picks the items 12, either singly or (preferably) in pairs, off the first conveyor belt 50, and delivers them to a pallet 14 that has arrived at the loading station 34, and that has been raised by the raising mechanism 18, 20. The first pick and place mechanism 52 may be of conventional design, well-known in the art, and need not be described in detail to understand the present invention. One suitable robotic device for use as the pick and place mechanism is the "Adept Cobra s800" SCARA robot, manufactured and sold by Adept Technology, Inc., of Livermore, Calif. Another suitable robotic device for this application is the Sony Model SRX-611 robot. Other equivalent robotic devices may be found that would be suitable for this application.

Typically, the first pick and place mechanism 52 includes first and second pivot arms 53a, 53b, extending horizontally from a fixed vertical support 54. The first pivot arm 53a has a first end pivotally connected to the support 54, and a second end to which the second pivot arm 53b is pivotally connected. Extending upwardly from the free end of the second pivot arm 53b is a cylinder 56 that accommodates a vertically reciprocating rod 58 surrounded by a hollow tube, the lower end of which terminates in a pneumatic pick-up head 60 connected by a flexible hose 62 to a pneumatic source (not shown). The reciprocating rod 58 and tube 59 may be moved between a lowered or extended position (FIG. 2) and a raised or retracted position (FIG. 3) by any conventional mechanism (e.g., pneumatic, electrical, electromagnetic) well-known in the art. Thus the rod 58 and the tube 59 are in the extended position when picking the items 12 off of the conveyor and when placing the items 12 on the pallet 14, and they are raised to its retracted position while the arms 53a, 53b are being pivoted between the first conveyor 50 and the pallet 14. The pick-up head 60 is advantageously configured to pick up and deposit the items 12 in pairs, but it may be configured for any desired number within practical limits.

Once the items 12 are loaded onto the pallet 14, the pallet 14 is moved by the turret 16 to the first printing station 36. The turret or turntable 16 is driven by an electric motor (not shown) that is controlled to advance its rotation incrementally and sequentially, from station to station, as the work or process step at each station is completed, as is well-known in the art.

Figure 6:
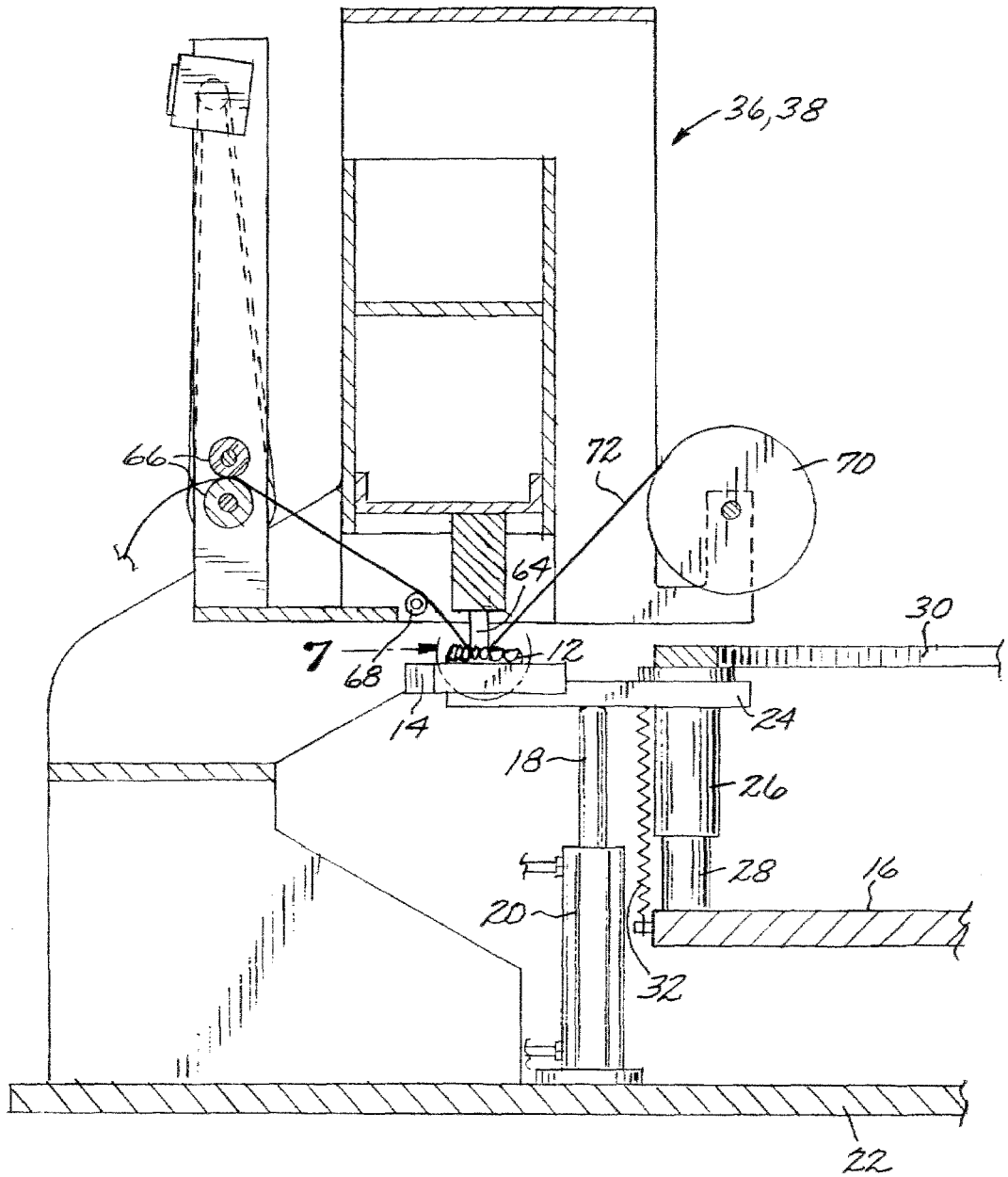
FIG. 6 is a cross-sectional view of an ink stamping station of the automated processing system, taken along line 6-6 of FIG. 1.
Figure 7:
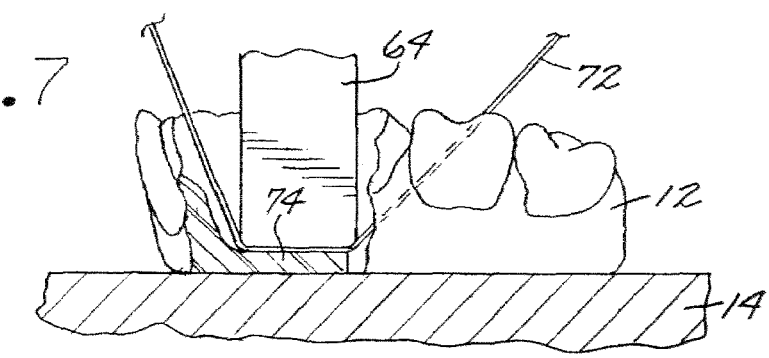
FIG. 7 is an enlarged detailed view of a print head, taken at location 7 of FIG. 6.
Figure 8:
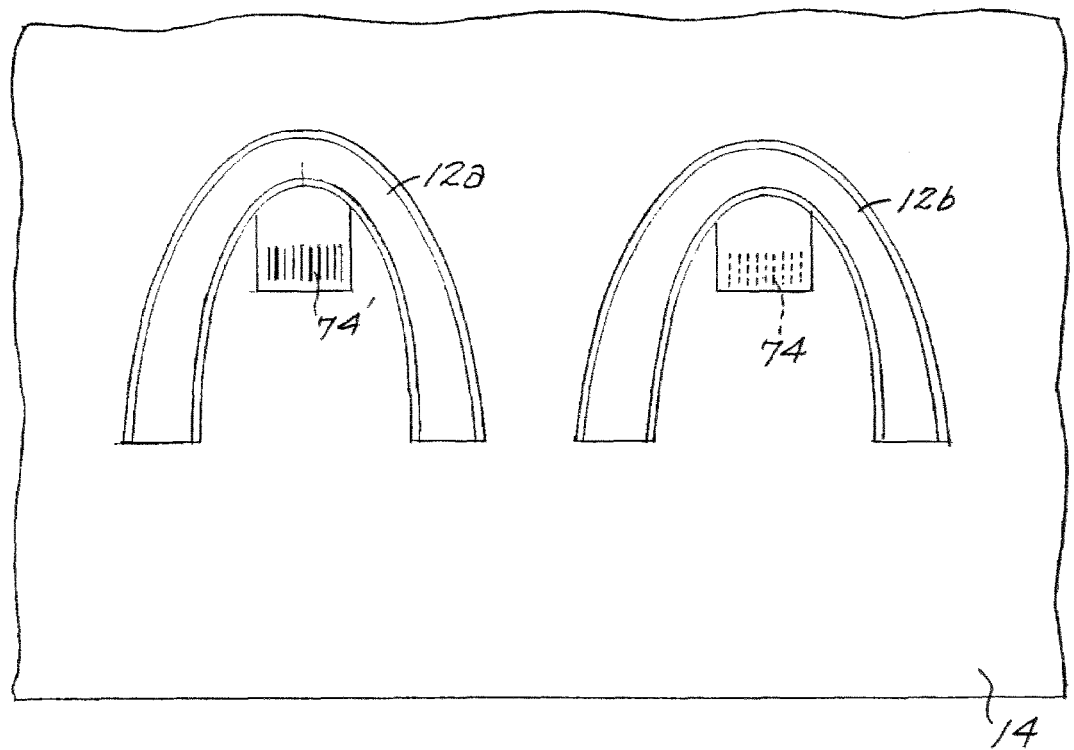
FIG. 8 is top plan view of a pair of dental aligner molds on a pallet after exiting the first printing station of the system of FIG. 1.
Figure 9:
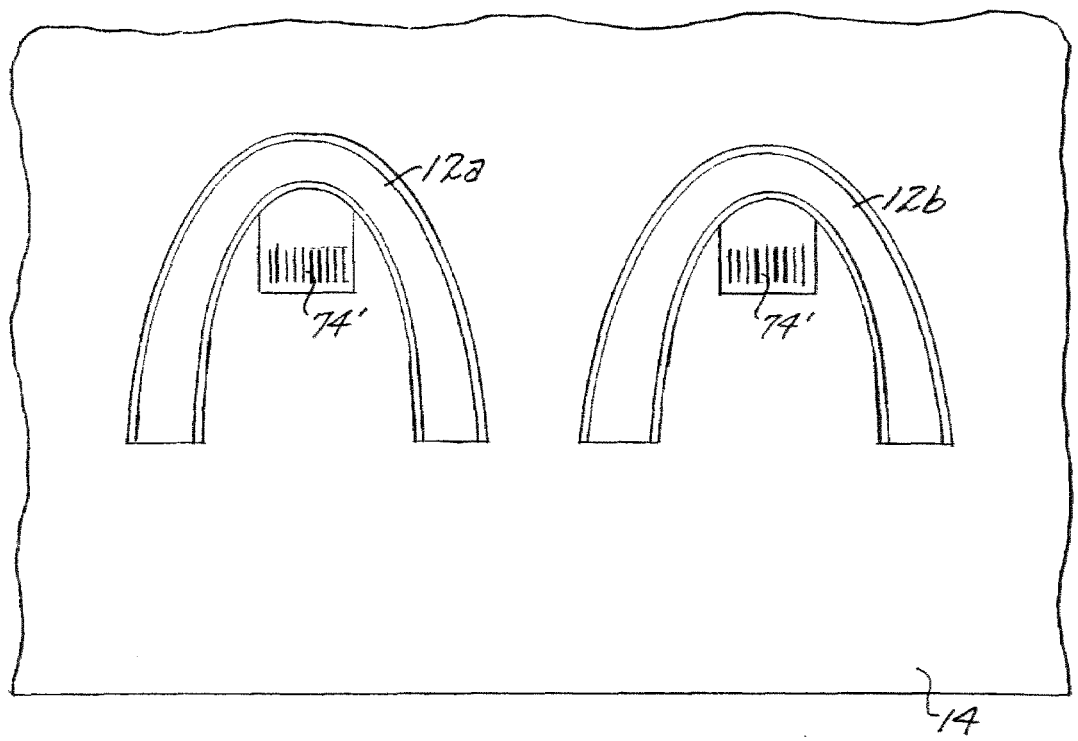
FIG. 9 is a top plan view of a pair of dental aligner molds on a pallet after the second printing station of the system of FIG. 1.

The first and second printing stations 36, 38 are substantially identical, and exemplary embodiments thereof are illustrated in FIGS. 6 and 7. Each of the printing stations 36, 38 is operable to apply an inked medium to a three-dimensional code formed in a predetermined area or part of each item 12. Each of the printing stations 36, 28 comprises a reciprocating stamping or printing head 64, a pair of pinch rollers 66, a guide roller 68, and a take-up reel 70. In a preferred embodiment, the ink medium is an inked foil in the form of a tape or ribbon 72 that is supplied from a supply reel or cartridge (not shown), and is then passed between the pinch rollers 66, over the guide roller 68, past the printing head 64, and then onto the take-up reel 70. The turret or turntable 16 stopped at a rotational position in which a first item 12a of the pair of items 12a, 12b on a pallet 14 is aligned under the printing head 64 of the first printing station 36. The pallet 14 is then raised relative to the turntable or turret 16 by the pallet-raising mechanism 18, 20 and the printing head 64 is then lowered, pressing the inked tape 72 against a three-dimensional data matrix (e.g., a three-dimensional barcode) 74 formed in the first of the pair of items 12 on the pallet 14, as shown in FIGS. 8 and 9. The data matrix 74 comprises a sequence or pattern of encoded data characters or data cells, and the ink is transferred from the tape or ribbon 72 to the data characters or data cells of the data matrix 74 by the application of heat to the printing head 64 while the tape or ribbon 72 is pressed between the printing head 64 and the data matrix 74. As a result, a layer of ink from the tape 72 is applied to the data matrix 74, so that the data encoded therein can be read by an optical reader, as will be discussed below.

FIG. 8 shows a plan view of the pallet 14 after exiting the first printing station 36, from which it can be seen that data matrix 74 of the first item 12a of the pair of items 12a, 12b is now an inked (and therefore optically visible) data matrix 74' (the not-yet-inked data matrix 74 of the second item 12b being shown in phantom), while FIG. 9 shows the pallet 14 after exiting the second printing station 38, in which the second item 12b now has an inked data matrix 74'. The second printing station 38 may advantageously include one or more air nozzles (not shown) that direct a jet of pressurized air at the freshly-inked data matrices 74, 74' to remove any ink that may "bridge" adjacent data characters or data cells as a result of the inking process.

The printing head 64 is preferably, but not necessarily, pneumatically operated. The pressure applied by the printing head 64 is controlled so to be maintained within a predetermined range, whereby the pressure is sufficient to assure the application of a readable inking, yet is not enough to damage the items. This printing pressure can be controlled by various means known in the art, such as a pressure transducer (not shown). If the measured printing pressure falls outside of the predetermined range, an alarm (not shown) is activated, and/or the system 10 will shut down. The upper and lower limits of the printing pressure will be dictated by the physical characteristics of the items to be printed, such as, for example, their material and their thickness in the area in which the data matrix 74 is located.

Once the first item 12a has been inked, the pallet 14 is lowered, and the turntable or turret 16 rotates past the idle station 48 (if present) and stops at the second printing station 38, where the pallet 14 is raised when the second item 12b of the pair of items 12a, 12b is aligned under the printing head 64, so that the data matrix 74 of the second item 12b can be inked, as discussed above and as shown in FIG. 9.

It will be appreciated that a single printing station may be employed, especially in the case where only a single item 12 is presented on the pallet 14. Alternatively, either of the printing stations may be modified, in ways that will readily suggest themselves to those skilled in the pertinent arts, to print two or more items simultaneously. As another alternative, three or more printing stations may be employed, each inking one or more of a like number of items on each pallet 14.

Figure 10:
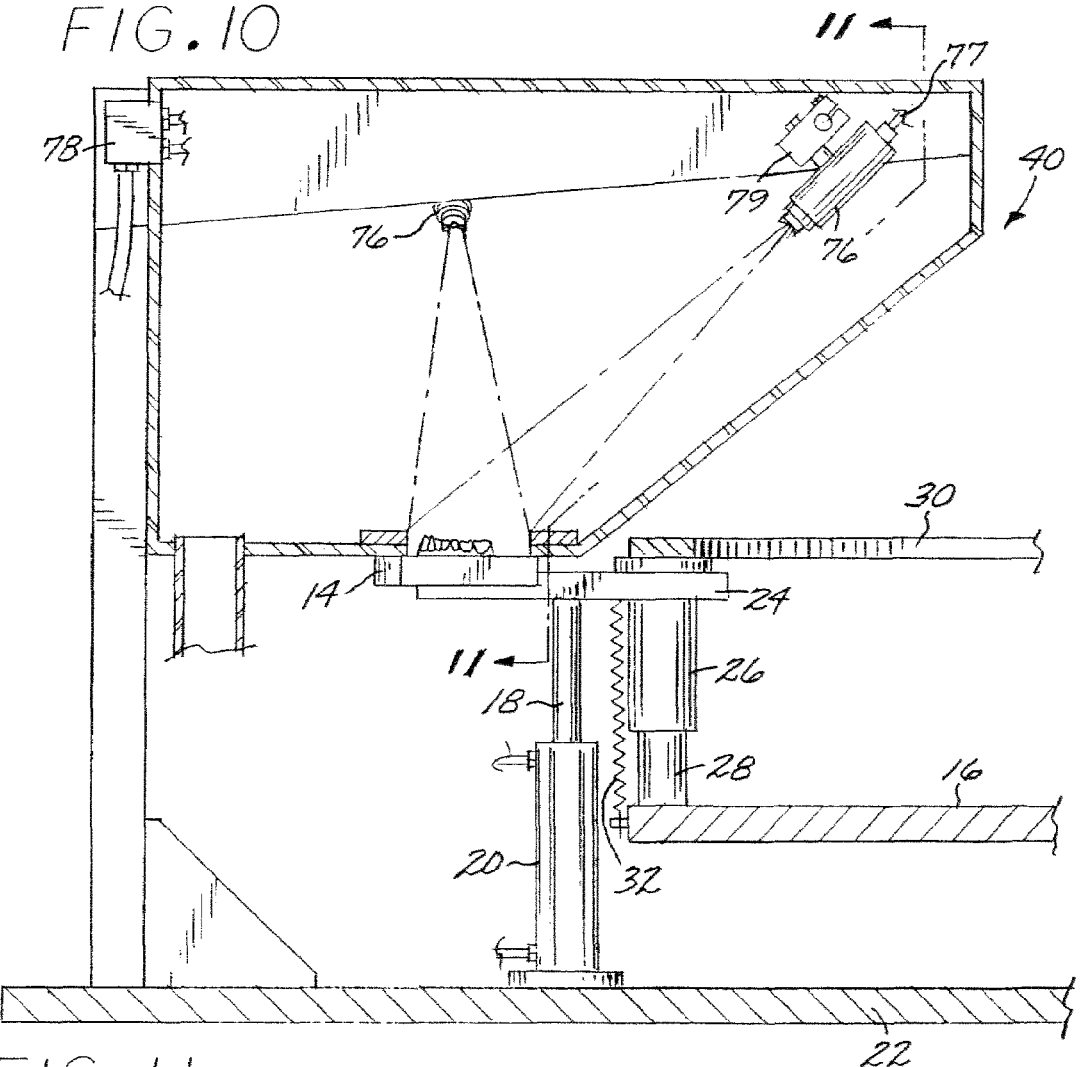
FIG. 10 is a cross-section view of a spraying station of the automated processing system, taken along line 10-10 of FIG. 1.
Figure 11:
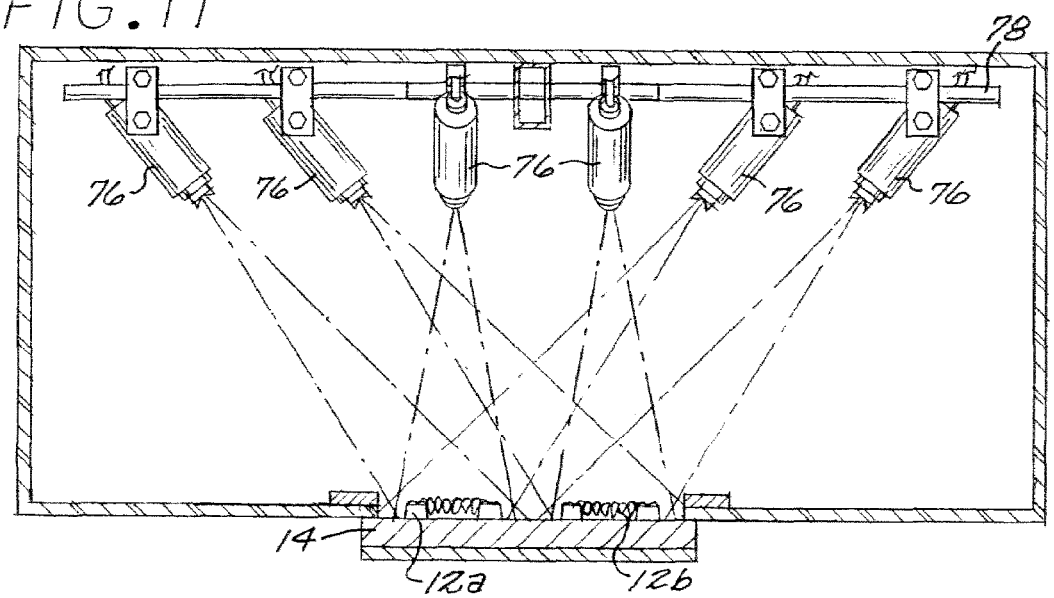
FIG. 11 is a cross-sectional view of the spraying station, taken along line 11-11 of FIG. 10.
Figure 12:
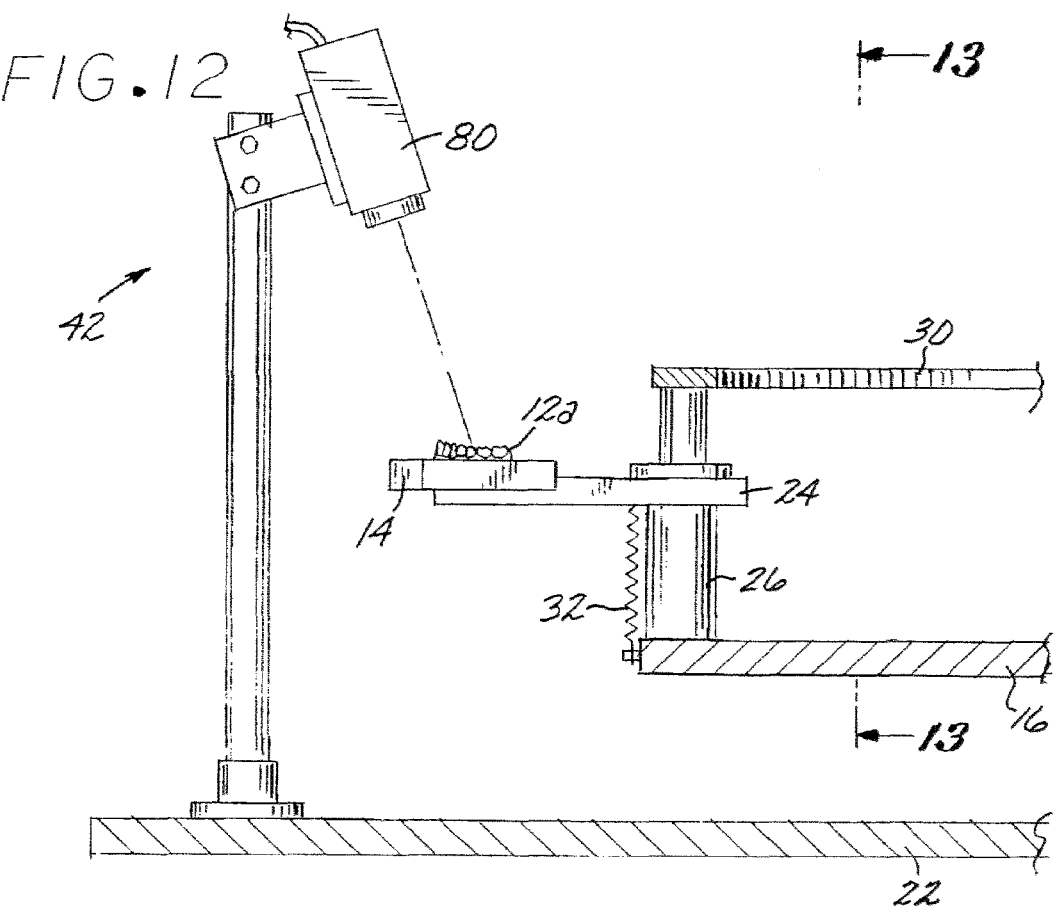
FIG. 12 is an elevational view, partly in cross-section, of a barcode reading station of the automated processing system, taken along line 12-12 of FIG. 1.
Figure 13:
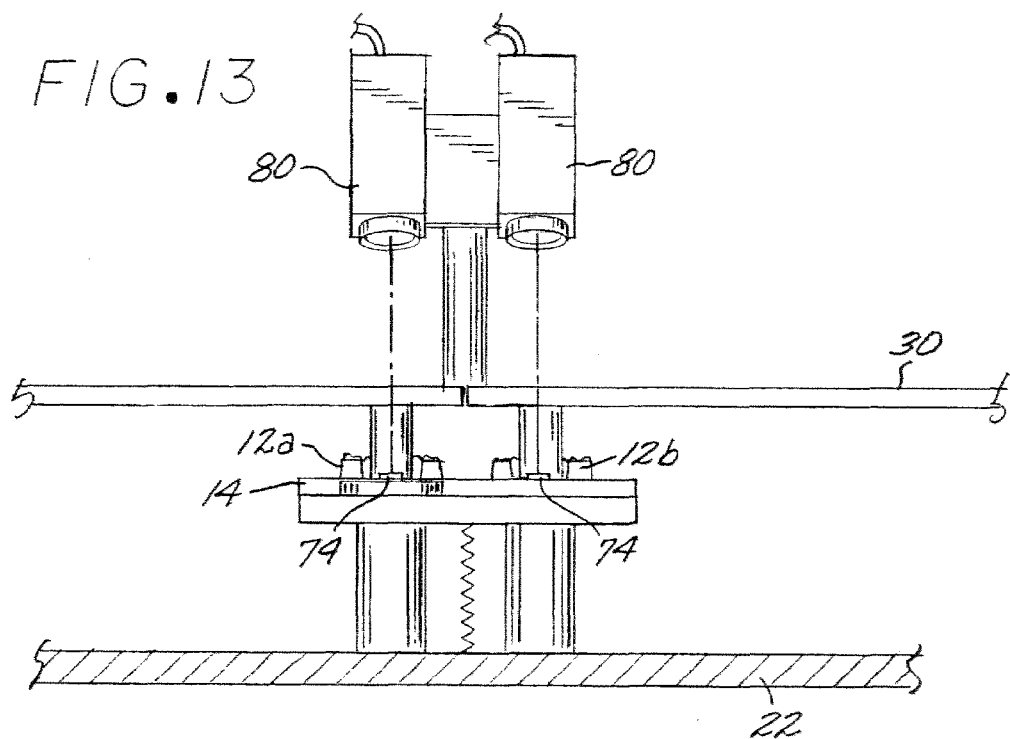
FIG. 13 is a cross-sectional view of the barcode reading station, taken along line 13-13 of FIG. 12.

After the data matrices 74 of the items 12a, 12b on the pallet 14 have been inked to render them optically readable, as described above, the pallet 14 is lowered, and the turntable or turret 16 rotates to move the pallet 14 to the liquid agent application station 40, an exemplary embodiment of which is shown in FIGS. 10 and 11. At the liquid agent application station 40, the turntable or turret 16 is stopped, and the pallet 14 is raised. A liquid agent (e.g., a silicone release agent) is then simultaneously applied to the items 12a, 11b, preferably by a spray applied through one or more spray heads 76. Preferably, there are at least four to six spray heads 76, with two or three spray heads 76 directed at various angles toward each of the items 12a, 12b, as shown in FIG. 11. The use of multiple spray heads 76 allows substantially the entire surface of each item 12a, 12b to be covered with the sprayed agent.

The application of the liquid agent is carefully controlled to assure that each item is adequately coated with the agent without wasting the agent. For example, the liquid agent is supplied to the spray heads 76 from a tank or reservoir (not shown) through tubing 77. Once the level of the release agent in the tank or reservoir reaches a predetermined minimum level, the spray station, an alarm (not shown) may be activated, and/or the liquid agent application station 40 is shut down to allow the tank or reservoir to be re-filled or replaced.

The operation of the spray heads 76 to assure proper application of the liquid agent is controlled by flow meters 78 and pressure transducers 79 that are operatively associated with the spray heads 76 to measure the flow rate and application pressure, respectively, of the sprayed agent. If either the measured flow rate or the measured spray pressure is above or below preset upper and lower flow rate and pressure limits, respectively, an alarm (not shown) may be activated, and/or the liquid agent application station 40 is shut down. The spray data (particularly the flow rate) for each spraying operation are advantageously conveyed by the appropriate transducer (s), through means such as a local area network (LAN), to a computer system (not shown) for storage in a system memory to create a spray parameter log for a predetermined time period. The log contains the spray data correlated to the time of each spray application, and it may be monitored to assure that each item is properly sprayed. From this information, any item that is determined to have had an insufficient spray agent application may be noted for special treatment and/or removal from the system.

Figure 14:
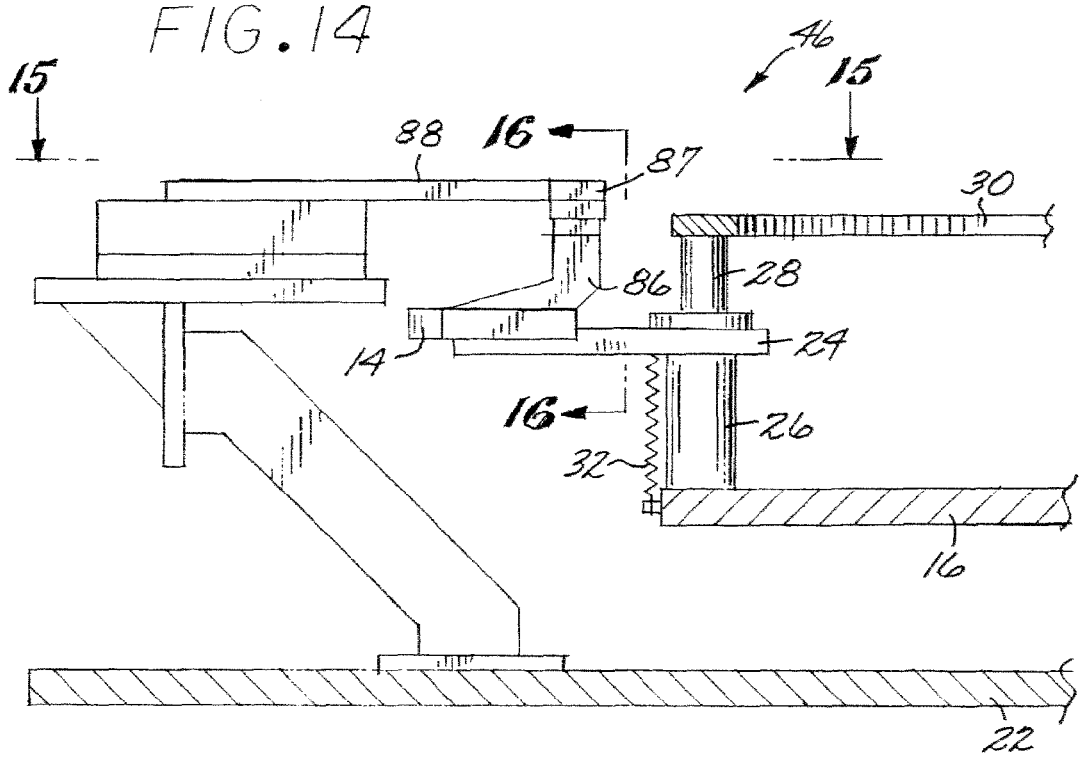
FIG. 14 is a cross-sectional view of a pallet cleaning station of the automated processing system, taken along line 14-14 of FIG. 1.
Figure 15:
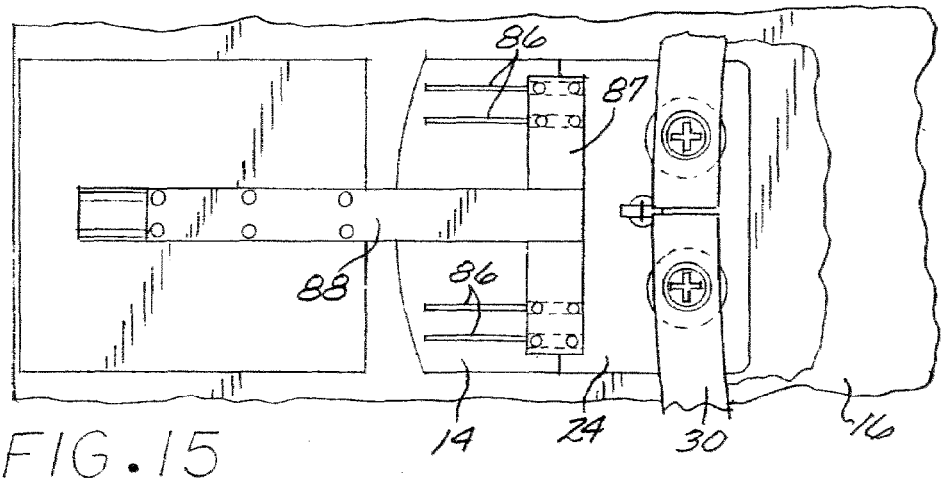
FIG. 15 is a top plan view of the pallet cleaning station, taken along line 15-15 of FIG. 14.

After spraying, the pallet 14 is lowered and the turntable or turret 16 is rotated to the barcode reading station 42, where the inked data matrices 74 are read by one or more (preferably two) optical readers 80 (e.g., vision cameras), as shown in FIGS. 14 and 15. The optical readers 80 read the information encoded in each data matrix 74, and they transmit electronic signals indicative of the information (e.g. by means of the above-noted LAN) to a memory-stored database in the above-noted computer system (not shown). This information can be used, for example, to verify information already stored in the database, or to enter new information into the database, or to compare the optically read information with pre-stored information in the database. For example, the read information may be used to verify that the items 12 on the pallet 14 are to be used in further manufacturing processes (e.g. dental aligner fabrication) to be performed that day.

It will be appreciated that code reading station 42 may be located before the liquid agent application station 40 (and after the printing stations 36, 38), rather than after the liquid agent application station.

After reading the data matrices 74 on the items 12 and extracting the encoded data, the turntable or turret 16 rotates the pallet 14 to the unloading station 44, where the items 12 are removed from the pallet 14 and placed on a second conveyor 82. At the unloading station 44, the pallet is raised to its raised position, as described above, and a second pick-and-place mechanism 84 (FIG. 1) removes the items 12 from the pallet 14 and places them on the second conveyor 82. The second pick-and-place mechanism 84 is substantially identical to the above-described first pick-and-place mechanism 52 employed in the above-described loading station 34, as shown in FIGS. 2-6. Accordingly, second the pick-and-place mechanism 84 employed at the unloading station 44 needs no further description. The second conveyor 82 may include RFID pallets 85, and the items 12, by virtue of identification information transmitted to the database at the reading station 44, may be mapped to a location/position on the RFID pallet 85. The mapped item positions may also be stored in the database, and, as the RFID pallets 85 are tracked, the computer system will "know" which items 12 are on each RFID pallet 85 on the second conveyor 82, and at which location on the RFID pallet 85.

Figure 16:
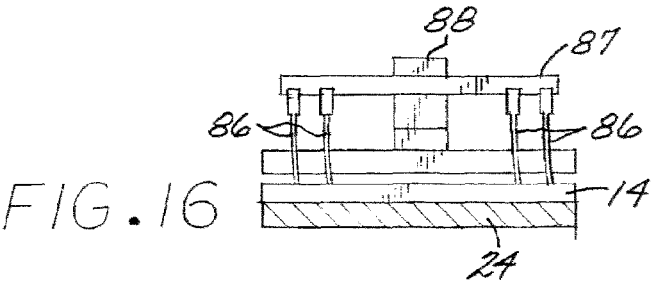
FIG. 16 is a cross-sectional view of the pallet cleaning station, taken along line 16-16 of FIG. 14.

After unloading the items 12 at the unloading station 44, the turntable or turret 16 is rotated to the cleaning station 46 (FIGS. 14-16), where the pallet 14 is wiped clean of any residual or excess spraying agent. The cleaning station 46 includes a plurality of wiper or scraper blades 86 attached to a cross-bar 87 at the end of a wiper pivot arm 88, which may be electrically or pneumatically operated. The pallet 14 is then returned to the loading station 34 by rotation of the turntable or turret 16.

Figure 17:
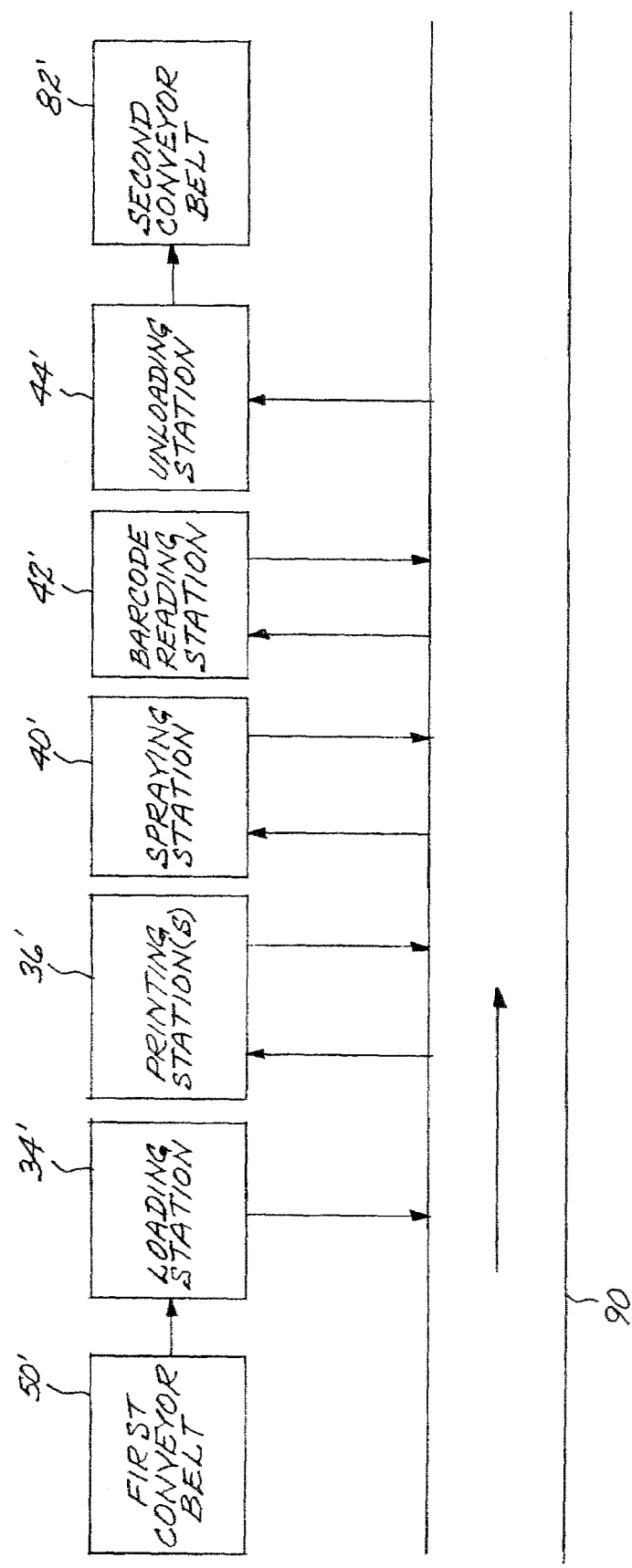
FIG. 17 is a diagrammatic view of an alternative embodiment of the system of the present invention, in which the stations of the system are arranged linearly.

FIG. 17 shows an alternate system 10' in accordance with another embodiment of the present invention. In this embodiment, the items are transported from a first conveyor line 50', incrementally through the several stations, to a second conveyor line 82', by a linear transport conveyor 90. In the context of this disclosure, the term "linear" is meant to include not only a straight line, but any arrangement in which the items are conveyed from the first conveyor to the second conveyor by a transport mechanism that has separate and non-contiguous starting and ending points, and that does not include a rotary turret or turntable and the like. Thus, the linear transport conveyor 90 may be a conveyor belt or line, or any suitable equivalent. In this embodiment, a loading station 34' picks items off of the first conveyor 50', and places them on the linear transport conveyor 90. The items are transported to one or more printing stations 36', where the barcodes are inked as described above. From there, the items are delivered to a liquid agent application station 40' for the application of a sprayed agent, as described above. The items are delivered to a code reading station 42' for the scanning of the inked barcodes, as described above. As in the above described rotary embodiment, the places of the code reading station and the liquid agent application station may be switched. Finally, the items are delivered to an unloading station 44', at which they are picked off of the line 90 and placed on the second conveyor 82'. Optionally, the linear transport conveyor 90 may be cleaned by a cleaning station (not shown) to remove residual sprayed agent.

The systems 10, 10' of the present invention are operated with a software algorithm that controls the various stations and that controls the rotation of the turntable or turret 16 or the motion of the linear transport conveyor 90 so as to allow each station to perform its intended operation while the turntable or turret or linear transport conveyor is stopped at that station. Such software is in a class of automation software that is well-known in the art, and its specific details would depend on the particular type of equipment or mechanism provided at each of the stations in the system.

While the present invention is described above with respect to what is currently considered as preferred embodiments, it is to be understood that the invention is not limited to the above description. For example, the application of the liquid agent to the items, if performed at all, may be performed by means other than spraying, such as dipping or brushing or any other suitable process that may suggest itself. Likewise, the inking of the barcodes may be performed by brushing or any other suitable process that is known in the art or that may subsequently suggest itself. Such modifications, variations, and uses of equivalent mechanisms and processes are deemed to be within the spirit and scope of the present invention, as defined in the appended claims.

What is claimed is:

1. A system for the automated processing of items, each of which incorporates information encoded in a three-dimensional data matrix formed on the surface of the item, the system comprising:
    a printing mechanism operable to apply an ink medium to the three-dimensional data matrix to render the three-dimensional data matrix into an optically-readable code on the surface of the item;
    a code-reading mechanism operable to read the optically readable code and to transmit a signal indicative of the optically-readable code to a database; and
    a transport mechanism operable to transport the items from the printing mechanism to the code-reading mechanism.

2. The system of claim 1, wherein the transport mechanism includes a rotary turntable.

3. The system of claim 1, wherein the transport mechanism is a linear transport mechanism.

4. The system of claim 1, wherein the printing mechanism comprises:
    a ribbon or tape provided with the ink medium; and
    a stamping head operable to press the ribbon or tape against the three-dimensional data matrix of an item when the item is transported to the printing mechanism.

5. The system of claim 1, further comprising a liquid agent application mechanism operable to apply a liquid agent to each item after the printing mechanism has applied the inking medium.

6. The system of claim 1, wherein the transport mechanism includes a plurality of pallets on which the items are placed for transport to the printing mechanism, and from the printing mechanism to the code-reading mechanism.

7. The system of claim 6, further comprising a loading station operable to place at least one item onto each of the pallets.

8. The system of claim 5, wherein the liquid agent application mechanism includes a spray head operable to spray the liquid agent onto the items.

9. The system of claim 4, wherein the stamping head is operable at a stamping pressure that is maintained within a predetermined pressure range.

10. A method for the automated processing of items, each of which incorporates information encoded in a three-dimensional data matrix formed on the surface of the item, the method comprising:

applying an ink medium to the three-dimensional data matrix to render the three-dimensional data matrix into an optically readable code on the surface of the item;

optically scanning the optically readable code to create an electronic signal indicative of the optically-readable code; and transmitting the signal to a computer database.

11. The method of claim 10, further comprising applying a liquid agent to the item after the inked medium has been applied to the three-dimensional data matrix.

12. The method of claim 11, further comprising applying a liquid agent to the item after the optically-readable code has been scanned.

13. The method of claim 11, wherein the liquid agent is applied by spraying.

14. The method of claim 13, wherein the spraying is performed at controlled pressure and flow rate.

15. The method of claim 12, wherein the liquid agent is applied by spraying.

16. The method of claim 15, wherein the spraying is performed at controlled pressure and flow rate.

17. The method of claim 10, wherein the ink medium is applied by pressing an inked tape or ribbon against the three-dimensional data matrix.

18. The method of claim 10, wherein the items are processed in pairs, and wherein the ink medium is first applied to the three-dimensional data matrix of a first one of each pair, and then applied to the three-dimensional data matrix of a second one of each pair.

19. The method of claim 18, further comprising applying a liquid agent to the items in each pair simultaneously after the ink medium is applied to the three-dimensional data matrix of the second item in each pair.

20. The method of claim 19, wherein the liquid agent is applied by spraying.

21. The method of claim 20, wherein the spraying is performed at controlled pressure and flow rate.

22. A system for the automated processing of items, each of which incorporates information encoded in a three-dimensional data matrix formed on the surface of the item, the system comprising:

a plurality of movable pallets;

a loading mechanism operable to load at least one item on each of the pallets as each pallet is moved to the loading mechanism;

a printing mechanism operable to apply an ink medium to the three-dimensional data matrix of each item on each pallet to render the three-dimensional data matrix into an optically-readable code on the surface of each item on a pallet when each pallet is moved to the printing mechanism;

a code-reading mechanism operable to read the optically readable code on the items on each pallet and to transmit a signal indicative of the optically-readable code to a database when each pallet is moved to the code-reading mechanism; and a transport mechanism operable to move each pallet from the loading mechanism to the printing mechanism, and from the printing mechanism to the code-reading mechanism.

23. The system of claim 22, wherein the loading mechanism is operable to load at least first and second items on each pallet, and wherein the printing mechanism is operable to apply the ink medium sequentially to the first item and then to the second item.

24. The system of claim 22, further comprising a liquid agent application mechanism that receives the pallets after the printing mechanism and that is operable to apply a liquid agent to each the item on each pallet.

25. The system of claim 23, further comprising a liquid agent application mechanism that receives the pallets after the printing mechanism and that is operable to apply a liquid agent to the first and second items simultaneously.

26. The system of claim 24, wherein the liquid agent application mechanism includes a spray head directed at each item on each pallet.

27. The system of claim 25, wherein the liquid agent application mechanism includes a spray head directed at each of the first and second items so as to spray the liquid agent onto each of the first and second items simultaneously.

28. The system of claim 22, further comprising an unloading mechanism, wherein the transport mechanism is operable to move each pallet from the code reading mechanism to the unloading mechanism, and wherein the unloading mechanism is operable to remove the at least one item from each of the pallets.

* * * * *

UNITED STATES PATENT AND TRADEMARK OFFICE
CERTIFICATE OF CORRECTION

PATENT NO. : 7,604,181 B2  Page 1 of 1
APPLICATION NO. : 11/617193
DATED : October 20, 2009
INVENTOR(S) : Culp et al.

It is certified that error appears in the above-identified patent and that said Letters Patent is hereby corrected as shown below:

In column 10, line 32, in Claim 24, after "each" insert --of--.

Signed and Sealed this

Second Day of February, 2010

David J. Kappos
*Director of the United States Patent and Trademark Office*